US007622275B2

(12) United States Patent
Fraissignes et al.

(10) Patent No.: US 7,622,275 B2
(45) Date of Patent: Nov. 24, 2009

(54) AEQUORIN AS A GROWTH MARKER IN YEAST

(75) Inventors: Pauline Fraissignes, Grand Quevilly (FR); Denis Guedin, Le Plessis Trevise (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/011,349

(22) Filed: Dec. 14, 2004

(65) Prior Publication Data

US 2005/0158816 A1 Jul. 21, 2005

Related U.S. Application Data

(62) Division of application No. 10/281,013, filed on Oct. 25, 2002, now abandoned.

(60) Provisional application No. 60/346,021, filed on Jan. 4, 2002.

(30) Foreign Application Priority Data

Oct. 27, 2001 (EP) ................................ 01125708

(51) Int. Cl.
*C12Q 1/02* (2006.01)
*C12Q 1/18* (2006.01)
*C12N 1/19* (2006.01)
*C12N 15/81* (2006.01)

(52) U.S. Cl. ....................... 435/32; 435/29; 435/254.2; 435/483

(58) Field of Classification Search ....................... None
See application file for complete search history.

(56) References Cited

U.S. PATENT DOCUMENTS 5,876,951 A 3/1999 Fowlkes et al.
2002/0025514 A1 * 2/2002 Jaworski et al. ................ 435/5

OTHER PUBLICATIONS

Nakajima-Shimada et al. Galactose-dependent expression of the recombinant Ca2(+)-binding photoprotein aequorin in yeast. Biochem Biophys Res Commun. Jan. 15, 1991;174(1):115-22, Jan. 1991.*

Inouye et al. Expression of apoaequorin complementary DNA in *Escherichia coli*. Biochemistry, vol. 25, pp. 8425-8429, 1986.*

Paz et al. Monitoring dynamics of gene expression in yeast during stationary phase. Gene, vol. 236, No. 1, pp. 33-42, Aug. 1999.*

Alber Tom et al., Nucleotide Sequence Of The Triose Phosphate Isomerase Gene Of *Saccharomyces cervisiae*, Journal Of Molecular And Applied Genetics, 1, (1982), pp. 419-434.

Brini Marisa et al., Targeted Recombinant Aequorins: Tools For Monitoring [Ca2+] In The Various Compartments Of A Living Cell, Microscopy Research And Technique (1999) 46 pp. 380-389.

Iida Hidetoshi et al., Essential Role For Induced Ca2+ Influx Followed By [Ca2+] Rise In Maintaining Viability Of Yeast Cells Late In the Mating Pheromone Response Pathway, The Journal Of Biological Chemistry (1990) 265 pp. 13391-13399.

Inouye Satoshi et al., Overexpression And Purification Of The Recombinant Ca2+ Binding Protein, Apoaequorin, J. Biochem (1989) 105 pp. 473-477.

Ito Hisao et al., Transformation Of Intact Yeast Cells Treated With Alkali Cations, Journal Of Bacteriology (1983) pp. 163-168.

Johnson Frank H. et al., Introduction To The Bioluminescence Of Medusae, With Special Reference To The Photoprotein Aequorin, Methods In Enzymology (1978) LVII pp. 1-653.

King Klim et al., Control Of Yeast Mating Signal Transduction By A Mammalian B2-Adrenergic Receptor And Gs Subunit, Erratum Appears In Science (1990) pp. 121-123.

Miller Andrew L. et al., Imaging [Ca2+]i With Aequorin Using A Photon Imaging Detector, Methods In Cell Biology (1994) 40 pp. 305-338.

Nakajima-Shimada Junko et al., Ca2+ Signal is Generated Only Once In the Mating Pheromone Response Pathway in *Saccharomyces cerevisiae*, Cell Structure and Functin 25, (2000) pp. 125-131.

Nakajima-Shimada Junko et al., Monitoring Of Intracellular Calcium In *Saccharomyces cerevisiae* With An Apoaequrin cDNA Expression System, Proc. Natl. Acad. Sci. USA, vol. 88, Cell Biology, Aug. 1991, pp. 6878-6882.

Ohimiya Yoshihiro et al., Shining The Light: The Mechanism Of The Bioluminescence Reaction Of Calcium-Binding Photoproteins, Chemistry & Biology (1996) 3 pp. 337-347.

Parnot Charles et al., Systematic Identification Of Mutations That Constitutively Activate The Angiotensin II Type 1A Receptor By Screening A Randomly Mutated cDNA Library With An Original Pharmacological Bioassay, PNAS, vol. 97, No. 13, Jun. 20, 2000, pp. 7615-7620.

Rizzuto Rosario et al., Rapid Changes Of Mitochondrial Ca2+ Revealed By Specifically Targeted Recombinant Aequorin, Nature (1992) 358 pp. 325-327.

Sheu Yeong-An et al., Measurement Of Intracellular Calcium Using Bioluminescent Aequorin Expressed In Human Cells, Analytical Biochemistry (1993) 209 pp. 343-347.

Shimomura Osamu et al., Peroxidized Coelenterazine, The Active Group In The Photoprotein Aequorin, Proc. Nat'l. Acad. Sci. USA (1978) 75 pp. 2611-2615.

Stables Jenny et al., Recombinant Aequorin As Reporter Of Changes In Intracellular Calcium In Mammalian Cells, Methods In Enzymology (2000) 327 pp. 456-471.

Thomas Andrew P. et al., The Use Of Fluorescent Indicators For Measurements Of Cytosolic-Free Calcium Concentration In Cell Populations And Single Cells, A Pratical Approach (McCormack JG and Cobbold PH eds) (1991) pp. 1-54.

Iida et al., Durable Synthesis of High Molecular Weight Heat Shock Proteins in Go Cells of the Yeast and Other Eucaryotes, J. of Cell Biology, vol. 99, Jul. 1984, pp. 199-207.

Tanahashi et al., Photoprotein aequorin: use as a reporter enzyme in studying gene expression in mammalian cells, Gene, vol. 96, 1990, pp. 249-255.

* cited by examiner

*Primary Examiner*—Christopher S. F. Low
*Assistant Examiner*—Jennifer Dunston

(57) ABSTRACT

A yeast cell containing constitutively expressed aequorin and methods of using the cells in growth and toxicity assays are disclosed.

2 Claims, 11 Drawing Sheets

Figure 1

```
                                      HindIII
                                      ~~~~~~~
  1   ATGACAAGCA AACAATACTC AGTCAAGCTT ACATCAGACT TCGACAACCC
      TACTGTTCGT TTGTTATGAG TCAGTTCGAA TGTAGTCTGA AGCTGTTGGG
 51   AAGATGGATT GGACGACACA AGCATATGTT CAATTTCCTT GATGTCAACC
      TTCTACCTAA CCTGCTGTGT TCGTATACAA GTTAAAGGAA CTACAGTTGG
101   ACAATGGAAA AATCTCTCTT GACGAGATGG TCTACAAGGC ATCTGATATT
      TGTTACCTTT TTAGAGAGAA CTGCTCTACC AGATGTTCCG TAGACTATAA
151   GTCATCAATA ACCTTGGAGC AACACCTGAG CAAGCCAAAC GACACAAAGA
      CAGTAGTTAT TGGAACCTCG TTGTGGACTC GTTCGGTTTG CTGTGTTTCT
201   TGCTGTAGAA GCCTTCTTCG GAGGAGCTGG AATGAAATAT GGTGTGGAAA
      ACGACATCTT CGGAAGAAGC CTCCTCGACC TTACTTTATA CCACACCTTT
251   CTGATTGGCC TGCATATATT GAAGGATGGA AAAAATTGGC TACTGATGAA
      GACTAACCGG ACGTATATAA CTTCCTACCT TTTTTAACCG ATGACTACTT
301   TTGGAGAAAT ACGCCAAAAA CGAACCAACG CTCATCCGTA TATGGGGTGA
      AACCTCTTTA TGCGGTTTTT GCTTGGTTGC GAGTAGGCAT ATACCCCACT
                 EcoRV
                 ~~~~~~
351   TGCTTTGTTT GATATCGTTG ACAAAGATCA AAATGGAGCC ATTACACTGG
      ACGAAACAAA CTATAGCAAC TGTTTCTAGT TTTACCTCGG TAATGTGACC
401   ATGAATGGAA AGCATACACC AAAGCTGCTG GTATCATCCA ATCATCAGAA
      TACTTACCTT TCGTATGTGG TTTCGACGAC CATAGTAGGT TAGTAGTCTT
451   GATTGCGAGG AAACATTCAG AGTGTGCGAT ATTGATGAAA GTGGACAACT
      CTAACGCTCC TTTGTAAGTC TCACACGCTA TAACTACTTT CACCTGTTGA
                                                     NcoI
                                                   ~~~~~~
                                                BamHI
                                                   ~~
501   CGATGTTGAT GAGATGACAA GACAACATTT AGGATTTTGG TACACCATGG
      GCTACAACTA CTCTACTGTT CTGTTGTAAA TCCTAAAACC ATGTGGTACC
      BamHI
      ~~~~
551   ATCCTGCTTG CGAAAAGCTC TACGGTGGAG CTGTCCCCTA A
      TAGGACGAAC GCTTTTCGAG ATGCCACCTC GACAGGGGAT T
```

Figure 4 (a)

Aequorin:

| Cells per well | $10^6$ | 500000 | 250000 | 125000 | 62500 | 31250 | 15625 | 7813 | 3906 | 1953 | 977 |
|---|---|---|---|---|---|---|---|---|---|---|---|
| | 213 | 149 | 93 | 50 | 29 | 18 | 10 | 6 | 3 | 2 | 1 |
| | 191 | 132 | 81 | 45 | 26 | 16 | 9 | 6 | 3 | 2 | 1 |
| | 199 | 145 | 89 | 53 | 32 | 19 | 10 | 6 | 3 | 2 | 2 |
| **Mean** | **201** | **142** | **88** | **49** | **29** | **18** | **10** | **6** | **3** | **2** | **1** |
| Stand. deviation | 11 | 9 | 6 | 4 | 3 | 1 | 0 | 0 | 0 | 0 | 0 |

β-Galactosidase (LacZ reporter):

| Cells per well | $10^6$ | 500000 | 250000 | 125000 | 62500 | 31250 | 15625 | 7813 | 3906 | 1953 | 977 |
|---|---|---|---|---|---|---|---|---|---|---|---|
| | 554 | 699 | 487 | 296 | 173 | 97 | 53 | 31 | 16 | 10 | 5 |
| | 435 | 522 | 372 | 220 | 125 | 65 | 35 | 20 | 11 | 6 | 3 |
| | 529 | 540 | 359 | 209 | 117 | 65 | 37 | 18 | 10 | 6 | 4 |
| **Mean** | **506** | **587** | **406** | **242** | **138** | **75** | **42** | **23** | **12** | **7** | **4** |
| Stand deviation | 63 | 98 | 71 | 47 | 31 | 19 | 10 | 7 | 3 | 2 | 1 |

See graphics on the next page.

Figure 4 (b)
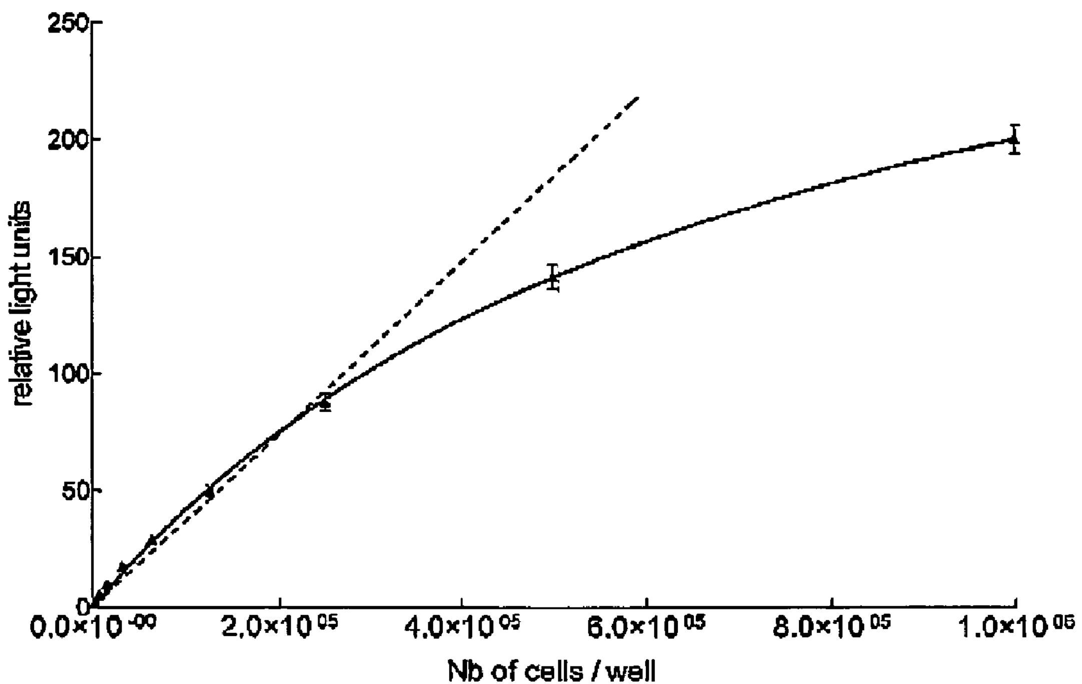
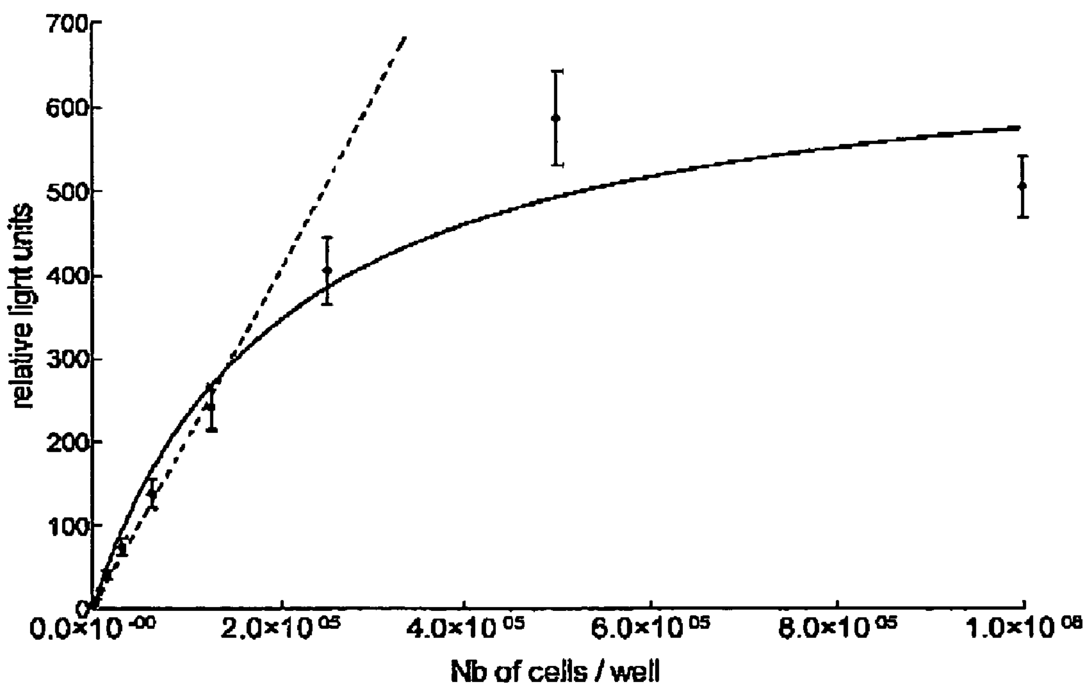

Figure 5
Aequorin
| | pYX132TPI-Aequorine | | mean | std deviation | pYX132TPI | | mean | std deviation |
|---|---|---|---|---|---|---|---|---|
| normal growth | 0.10 | 0.09 | 0.09 | 0.01 | 0.11 | 0.19 | 0.15 | 0.06 |
| toxic 100μM | 0.05 | 0.05 | 0.05 | 0.00 | 0.05 | 0.07 | 0.06 | 0.01 |
| w/o uracil | 0.06 | 0.05 | 0.05 | 0.01 | 0.05 | 0.05 | 0.05 | 0.00 |
lacZ
| | pYX132TPI-lacZ | | | | pYX132TPI | | | |
|---|---|---|---|---|---|---|---|---|
| normal growth | 0.18 | 0.19 | 0.19 | 0.00 | 0.16 | 0.12 | 0.14 | 0.03 |
| toxic 100μM | 0.06 | 0.06 | 0.06 | 0.00 | 0.05 | 0.06 | 0.06 | 0.01 |
| w/o uracil | 0.07 | 0.07 | 0.07 | 0.00 | 0.06 | 0.08 | 0.07 | 0.01 |
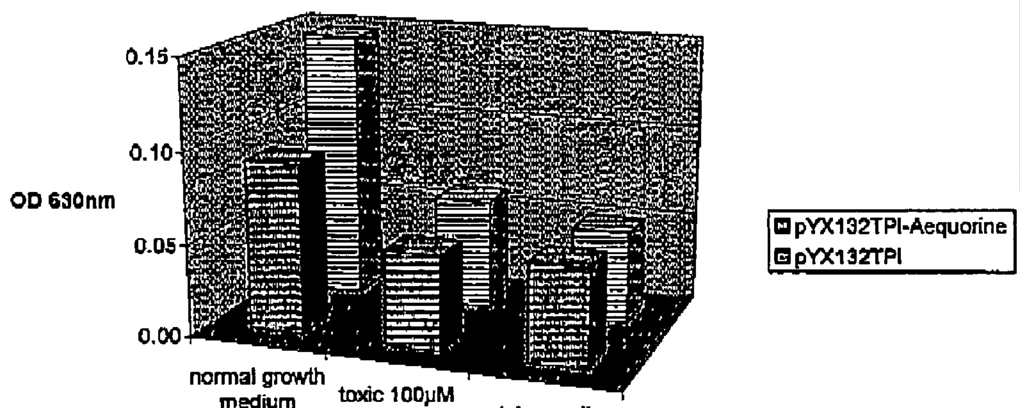
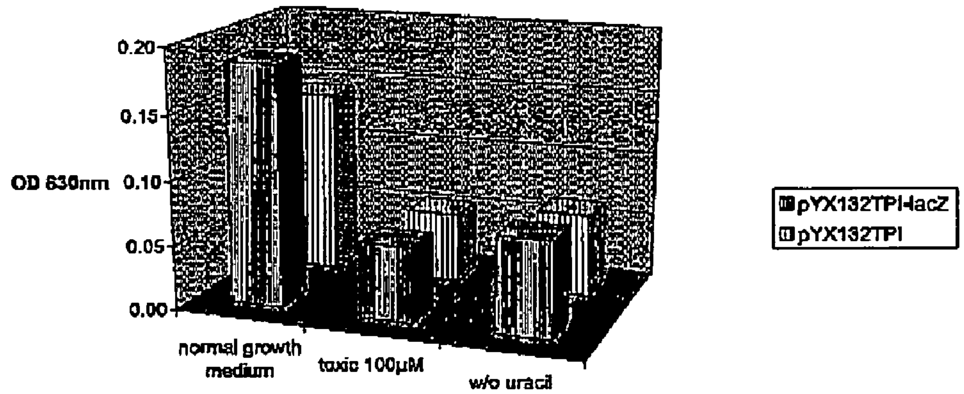

Figure 6
Aequorin
| | pYX132TPI-Aequorine | | mean | std deviation | pYX132TPI | | mean | std deviation |
|---|---|---|---|---|---|---|---|---|
| normal growth | 123 | 154 | **138** | 22 | 0 | 3 | **1** | 2 |
| toxic 100µM | 11 | 9 | **10** | 1 | 3 | 0 | **2** | 2 |
| w/o uracil | 19 | 13 | **16** | 4 | 1 | 1 | **1** | 0 |
lacZ
| | pYX132TPI-lacZ | | | | pYX132TPI | | | |
|---|---|---|---|---|---|---|---|---|
| normal growth | 260 | 292 | **276** | 23 | 0 | 0 | **0** | 0 |
| toxic 100µM | 101 | 131 | **116** | 21 | 0 | 0 | **0** | 0 |
| w/o uracil | 57 | 71 | **64** | 10 | 0 | 0 | **0** | 0 |
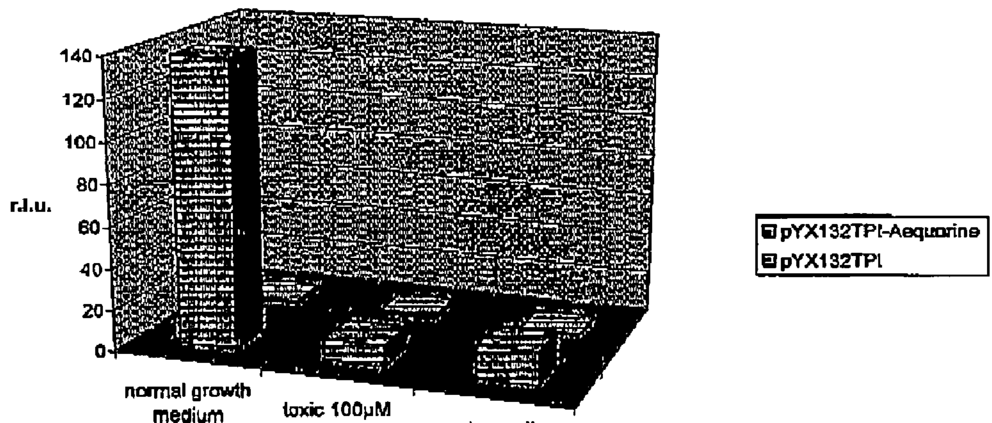
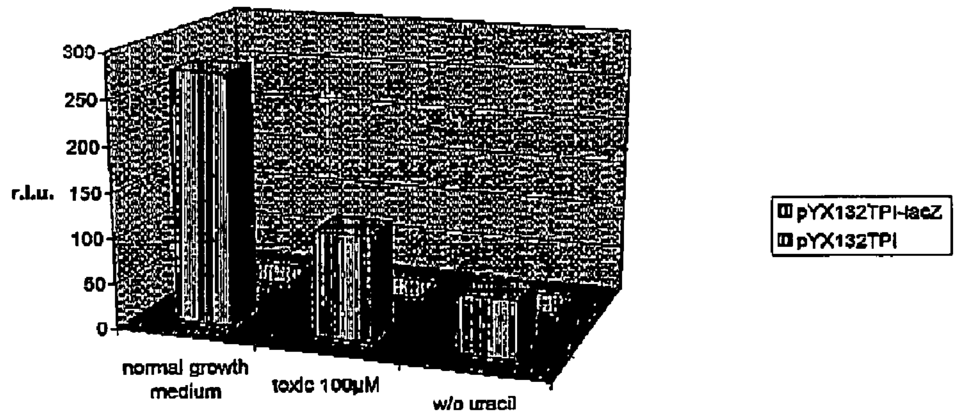

Figure 7
Aequorin
| | pYX132TPI-Aequorine | | mean | std deviation | pYX132TPI | | mean | std deviation |
|---|---|---|---|---|---|---|---|---|
| normal growth | 1.05 | 1.04 | 1.04 | 0.01 | 1.06 | 1.04 | 1.05 | 0.01 |
| toxic 100µM | 0.74 | 0.63 | 0.69 | 0.08 | 0.52 | 0.56 | 0.54 | 0.03 |
| w/o uracil | 0.06 | 0.06 | 0.06 | 0.00 | 0.05 | 0.07 | 0.06 | 0.01 |
lacZ
| | pYX132TPI-lacZ | | | | pYX132TPI | | | |
|---|---|---|---|---|---|---|---|---|
| normal growth | 1.06 | 1.04 | 1.05 | 0.01 | 1.06 | 1.05 | 1.06 | 0.01 |
| toxic 100µM | 0.56 | 0.59 | 0.57 | 0.03 | 0.62 | 0.79 | 0.71 | 0.12 |
| w/o uracil | 0.08 | 0.08 | 0.08 | 0.00 | 0.06 | 0.06 | 0.06 | 0.00 |
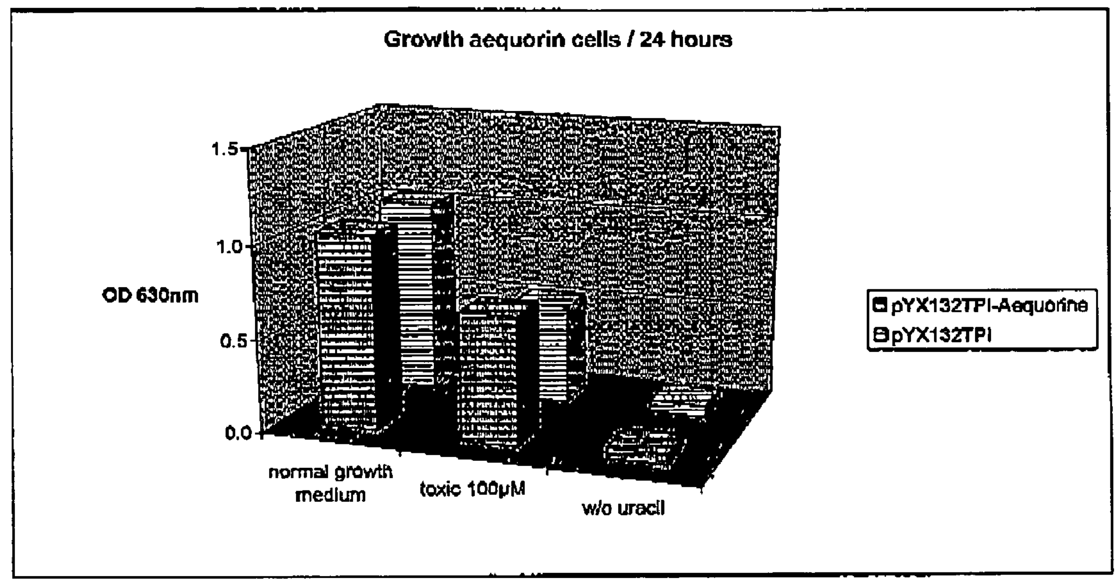
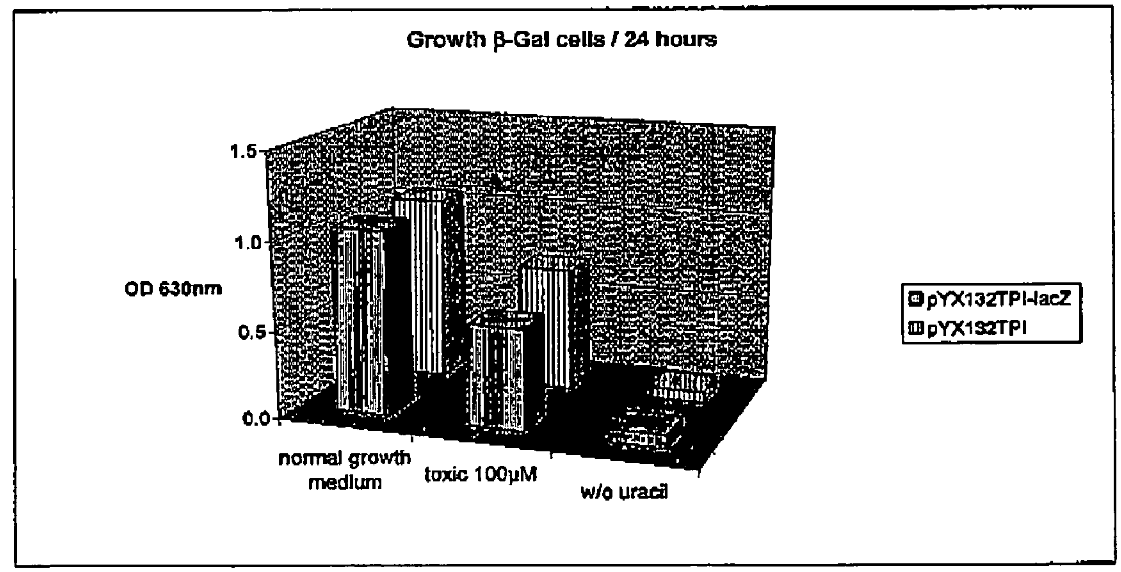

Figure 8
Aequorin
| | pYX132TPI-Aequorine | | mean | std deviation | pYX132TPI | | mean | std deviation |
|---|---|---|---|---|---|---|---|---|
| normal growth | 159 | 192 | **175** | 24 | 2 | 0 | 1 | 1 |
| toxic 100μM | 62 | 37 | **50** | 18 | 3 | 0 | 1 | 2 |
| w/o uracil | 10 | 11 | **10** | 0 | 10 | 0 | 5 | 7 |
lacZ
| | pYX132TPI-lacZ | | | | pYX132TPI | | | |
|---|---|---|---|---|---|---|---|---|
| normal growth | 2477 | 2073 | **2275** | 286 | 0 | 0 | 0 | 0 |
| toxic 100μM | 1902 | 1944 | **1923** | 30 | 0 | 0 | 0 | 0 |
| w/o uracil | 80 | 102 | **91** | 16 | 0 | 0 | 0 | 0 |
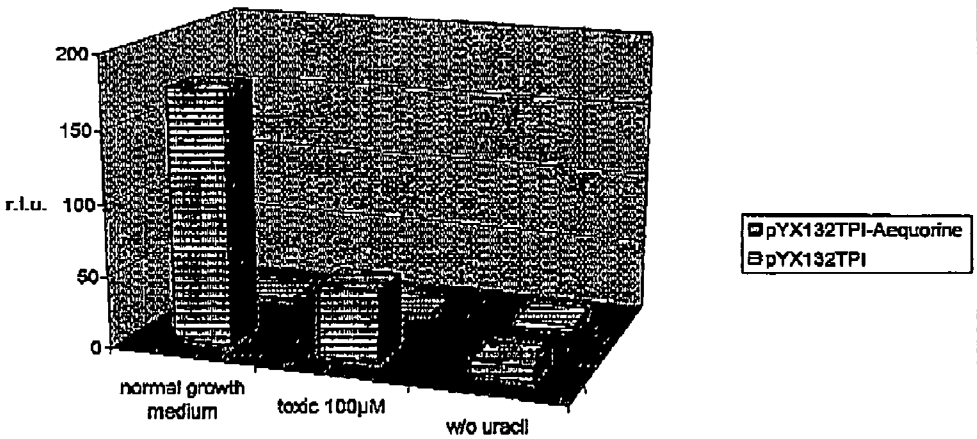
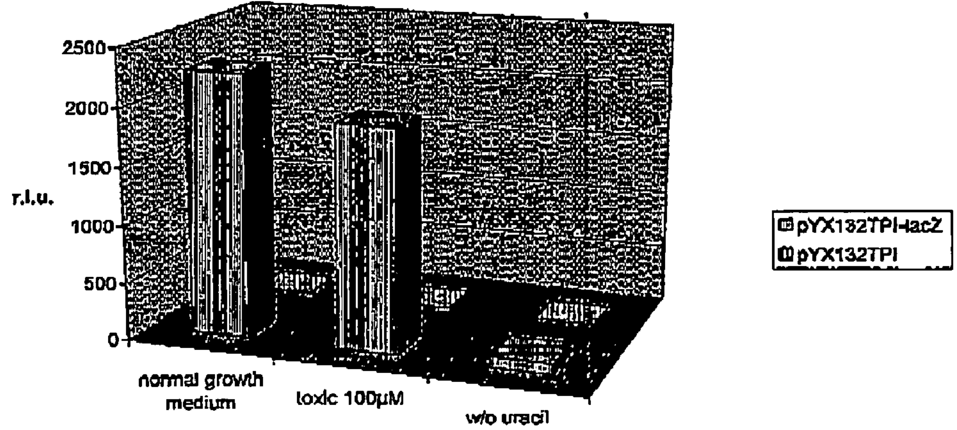

| Glucose | Control p425Gal-AEQ | | pGal-activated kinase + p425Gal-AEQ | |
|---|---|---|---|---|
| | 7 | 9 | 5 | 5 |
| | 8 | 9 | 5 | 6 |
| | 8 | 10 | 5 | 6 |
| Mean | 9 | | 6 | |
| Stand. deviation | 1 | | 1 | |
| **Galactose** | | | | |
| | 5455 | 8146 | 1 | 0 |
| | 6997 | 8548 | 0 | 0 |
| | 6148 | 9449 | 1 | 0 |
| Mean | 7457 | | 1 | |
| Stand. deviation | 1521 | | 0 | |

SEQUENCE LISTING

```
<160> NUMBER OF SEQ ID NOS: 4

<210> SEQ ID NO 1
<211> LENGTH: 591
<212> TYPE: DNA
<213> ORGANISM: Aequorea victoria
<220> FEATURE:
<221> NAME/KEY: CDS
<222> LOCATION: (1)..(591)
<223> OTHER INFORMATION:

<400> SEQUENCE: 1

atg aca agc aaa caa tac tca gtc aag ctt aca tca gac ttc gac aac       48
Met Thr Ser Lys Gln Tyr Ser Val Lys Leu Thr Ser Asp Phe Asp Asn
1               5                   10                  15

cca aga tgg att gga cga cac aag cat atg ttc aat ttc ctt gat gtc       96
Pro Arg Trp Ile Gly Arg His Lys His Met Phe Asn Phe Leu Asp Val
            20                  25                  30

aac cac aat gga aaa atc tct ctt gac gag atg gtc tac aag gca tct      144
Asn His Asn Gly Lys Ile Ser Leu Asp Glu Met Val Tyr Lys Ala Ser
        35                  40                  45

gat att gtc atc aat aac ctt gga gca aca cct gag caa gcc aaa cga      192
Asp Ile Val Ile Asn Asn Leu Gly Ala Thr Pro Glu Gln Ala Lys Arg
    50                  55                  60

cac aaa gat gct gta gaa gcc ttc ttc gga gga gct gga atg aaa tat      240
His Lys Asp Ala Val Glu Ala Phe Phe Gly Gly Ala Gly Met Lys Tyr
65                  70                  75                  80

ggt gtg gaa act gat tgg cct gca tat att gaa gga tgg aaa aaa ttg      288
Gly Val Glu Thr Asp Trp Pro Ala Tyr Ile Glu Gly Trp Lys Lys Leu
                85                  90                  95

gct act gat gaa ttg gag aaa tac gcc aaa aac gaa cca acg ctc atc      336
Ala Thr Asp Glu Leu Glu Lys Tyr Ala Lys Asn Glu Pro Thr Leu Ile
            100                 105                 110
```

-continued

```
cgt ata tgg ggt gat gct ttg ttt gat atc gtt gac aaa gat caa aat      384
Arg Ile Trp Gly Asp Ala Leu Phe Asp Ile Val Asp Lys Asp Gln Asn
        115                 120                 125

gga gcc att aca ctg gat gaa tgg aaa gca tac acc aaa gct gct ggt      432
Gly Ala Ile Thr Leu Asp Glu Trp Lys Ala Tyr Thr Lys Ala Ala Gly
    130                 135                 140

atc atc caa tca tca gaa gat tgc gag gaa aca ttc aga gtg tgc gat      480
Ile Ile Gln Ser Ser Glu Asp Cys Glu Glu Thr Phe Arg Val Cys Asp
145                 150                 155                 160

att gat gaa agt gga caa ctc gat gtt gat gag atg aca aga caa cat      528
Ile Asp Glu Ser Gly Gln Leu Asp Val Asp Glu Met Thr Arg Gln His
                165                 170                 175

tta gga ttt tgg tac acc atg gat cct gct tgc gaa aag ctc tac ggt      576
Leu Gly Phe Trp Tyr Thr Met Asp Pro Ala Cys Glu Lys Leu Tyr Gly
            180                 185                 190

gga gct gtc ccc taa                                                  591
Gly Ala Val Pro
        195


<210> SEQ ID NO 2
<211> LENGTH: 196
<212> TYPE: PRT
<213> ORGANISM: Aequorea victoria

<400> SEQUENCE: 2

Met Thr Ser Lys Gln Tyr Ser Val Lys Leu Thr Ser Asp Phe Asp Asn
1               5                   10                  15

Pro Arg Trp Ile Gly Arg His Lys His Met Phe Asn Phe Leu Asp Val
            20                  25                  30

Asn His Asn Gly Lys Ile Ser Leu Asp Glu Met Val Tyr Lys Ala Ser
        35                  40                  45

Asp Ile Val Ile Asn Asn Leu Gly Ala Thr Pro Glu Gln Ala Lys Arg
    50                  55                  60

His Lys Asp Ala Val Glu Ala Phe Phe Gly Gly Ala Gly Met Lys Tyr
65                  70                  75                  80

Gly Val Glu Thr Asp Trp Pro Ala Tyr Ile Glu Gly Trp Lys Lys Leu
                85                  90                  95

Ala Thr Asp Glu Leu Glu Lys Tyr Ala Lys Asn Glu Pro Thr Leu Ile
            100                 105                 110

Arg Ile Trp Gly Asp Ala Leu Phe Asp Ile Val Asp Lys Asp Gln Asn
        115                 120                 125

Gly Ala Ile Thr Leu Asp Glu Trp Lys Ala Tyr Thr Lys Ala Ala Gly
    130                 135                 140

Ile Ile Gln Ser Ser Glu Asp Cys Glu Glu Thr Phe Arg Val Cys Asp
145                 150                 155                 160

Ile Asp Glu Ser Gly Gln Leu Asp Val Asp Glu Met Thr Arg Gln His
                165                 170                 175

Leu Gly Phe Trp Tyr Thr Met Asp Pro Ala Cys Glu Lys Leu Tyr Gly
            180                 185                 190

Gly Ala Val Pro
        195


<210> SEQ ID NO 3
<211> LENGTH: 62
<212> TYPE: DNA
<213> ORGANISM: Artificial Sequence
<220> FEATURE:
<223> OTHER INFORMATION: PCR Primer
```

-continued

```
<400> SEQUENCE: 3

ccggaattcc ggatgacaag caaacaatac tcagtcaagc ttacatcaga cttcgacaac     60

cc                                                                    62


<210> SEQ ID NO 4
<211> LENGTH: 30
<212> TYPE: DNA
<213> ORGANISM: Artificial Sequence
<220> FEATURE:
<223> OTHER INFORMATION: PCR primer

<400> SEQUENCE: 4

gggccttagg ggacagctcc accgtagagc                                      30
```

AEQUORIN AS A GROWTH MARKER IN YEAST

FIELD OF THE INVENTION

The present invention relates to a modified yeast cell containing aequorin as a growth marker—methods of making and methods of using such modified yeast cells.

BACKGROUND OF THE INVENTION

Aequorin is a photoprotein isolated from luminescent jellyfish *Aequoria victoria.*

Apoaequorin is a protoprotein which, upon binding to coelenterazine, can emit photons in the presence $Ca^{2+}$. The Aequorin complex comprises a 22,514 MW Apoaequorin protein (SEQ ID NO: 2), molecular oxygen and the luminophore coelenterazine (Inouye et al., 1989; Johnson and Shimomura, 1978; Shimomura and Johnson, 1978). When three $Ca^{2+}$ ions bind to this complex, coelenterazine is oxidized to coelenteramide, with a concomitant release of carbon dioxide and blue light (emission maximum ~466 nm) (FIG. 10).

Because of its $Ca^{2+}$-dependent luminescence, the Aequorin complex has been extensively used as an intracellular $Ca^{2+}$ indicator detected by chemiluminescence assay.

Aequorin reportedly does not disrupt cell functions or embryo development (Miller et al., 1994).

Aequorin can be easily expressed in mammalian cells. It has been utilized to monitor the cytosolic-free calcium concentration (Thomas and Delaville, 1991) (Sheu et al., 1993) (Stables et al., 2000).

Aequorin can also be easily targeted to specific organelles such as mitochondria (Brini et al., 1999) (Rizzuto et al., 1992) to monitor different aspects of calcium homeostasis.

The pharmaceutical industry has taken wide advantage of the different properties of Aequorin, particularly in High Throughput Screens (Detheux, 2000). The activation of a receptor coupled to the phospholipase C transduction pathway can be easily detected in presence of the photoprotein Aequorin, because of an instantaneous release of calcium from the endoplasmic reticulum. WO0002045, Detheux et al. (EUROSCREEN S.A.) describes a high-throughput screening diagnostic and/or dosage method of an agonist and/or an antagonist for a calcium-coupled receptor (in mammalian cells) where Aequorin is used as marker for intracellular calcium changes upon receptor stimulation.

It has been previously shown that Aequorin can be functionally expressed in yeast and detected. Nakajima-Shimada et al. (Nakajima-Shimada et al., 1991b) describe the monitoring of intracellular calcium in *Saccharomyces cerevisiae* with an Apoaequorin cDNA expression system. Here, Aequorin was again used as a marker of intracellular calcium upon stress or glucose variations in the medium.

In contrast to mammalian signal transduction, there is no comparable $Ca^{2+}$ release from the endoplasmic reticulum upon G protein-coupled receptor (GPCR) activation in yeast cells. The addition of α-factor to a yeast cell (i.e. stimulation of the GPCR Ste2) raises $[Ca^{2+}]i$ from a basal level of approximately 100 nM to a few hundred nanomolar in the cells, simultaneous with the induction of $Ca^{2+}$ influx. When the cells are incubated with α-factor in a $Ca^{2+}$-deficient medium, $Ca^{2+}$ influx is greatly reduced, and the rise in $[Ca^{2+}]i$ is not detected (Iida et al., 1990). This slight variation in cytosolic $[Ca^{2+}]$ does not interfere with pathway activity detection according to the instant invention.

A limited number of reporter genes are known for use in the yeast cells, such as *Saccharomyces cerevisiae*, and their use is not always appropriate as a growth marker. Accordingly, there is a continuing need for additional yeast reporter gene systems optimized use as a growth marker.

For purposes of being used as a growth marker, a reporter gene product must be easy to detect. Accordingly, the most commonly utilized reporter gene in yeast is LacZ, which encodes the very big and stable enzyme β-Galactosidase, which is detected in a chemiluminescence assay. However, bacterial contamination may occur in yeast cultures during assays and most of the contaminants physiologically express a β-Galactosidase activity. Contaminated cultures give a very strong signal in the presence of β-Galactosidase substrates, leading to false results in growth assays.

SUMMARY OF THE INVENTION

A yeast cell is provided, containing an aequorin-encoding deoxyribonucleic acid sequence expressibly linked to a constitutive yeast promoter.

The invention also provides a method of measuring the growth rate of a yeast cell culture, the method having the steps:

(a) providing a yeast cell having an aequorin-encoding deoxyribonucleic acid sequence expressibly linked to a constitutive yeast promoter,
(b) incubating the yeast cell, and
(c) measuring the amount of aequorin produced during the incubation.

In addition, the invention provides a method for determining growth-regulating or toxic effects of a compound on a yeast cell culture, the method having the steps:

(a) providing a yeast cell having an aequorin-encoding deoxyribonucleic acid sequence expressibly linked to a constitutive yeast promoter,
(b) incubating the yeast cell with the compound,
(c) measuring the amount of aequorin produced during the incubation, and
(d) comparing the measured amount of aequorin produced with that amount of aequorin produced by a similar yeast culture incubated in the absence of the compound.

BRIEF DESCRIPTION OF THE DRAWINGS

FIG. 1: Aequorin—open reading frame (SEQ ID NO: 1)

FIG. 4(*a*) and (*b*): Results of cell serial dilution—Linearity

FIG. 5: Results of growth experiments—Yeast growth after 5 hours

FIG. 6: Results of growth experiments—Reporter detection after 5 hours

FIG. 7: Results of growth experiments—Yeast growth after 24 hours

FIG. 8: Results of growth experiments—Reporter detection after 24 hours

DETAILED DESCRIPTION OF THE INVENTION

Figure 2:
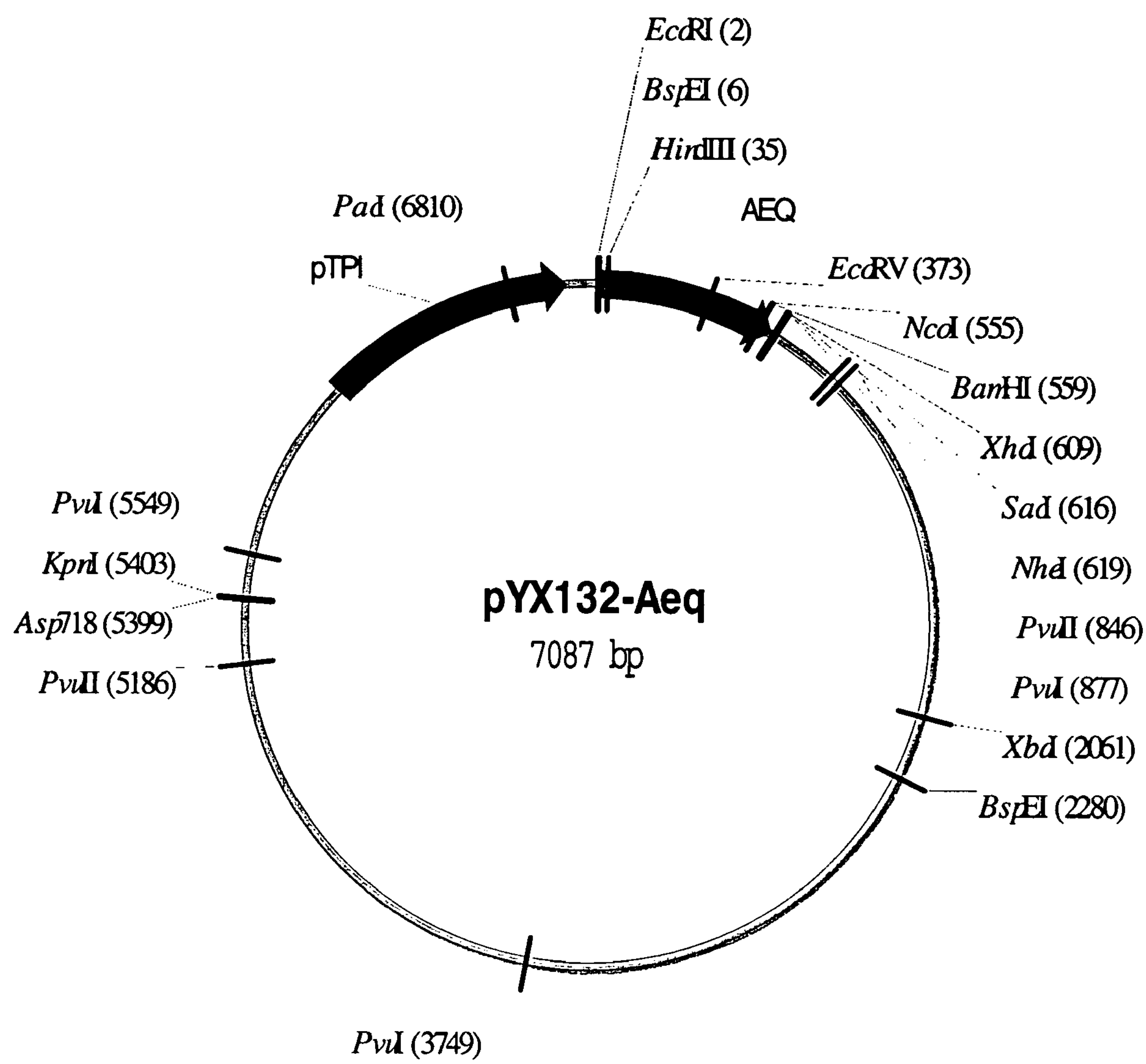
FIG. 2: Restriction map of pYX132TPI-Aequorin

Aequorin is a photoprotein detected, like β-Galactosidase, in a chemiluminescence assay. As Aequorin (22514 MW) is five times smaller than β-Galactosidase (116351 MW), it can accumulate in a greater amount to give a higher sensitivity to an assay of the growth rate of a yeast culture. Also, aequorin has a shorter half-life than β-Galactosidase. Therefore Aequorin is more suitable for growth/growth arrest quantification assays.

Aequorin can be expressed functionally by the yeast *S. cerevisiae* (Nakajima-Shimada et al., 1991a).

Aequorin is easily detected in a luminescent assay, in presence of coelenterazin and $Ca^{2+}$.

So far Aequorin has not been utilized as growth marker permanently expressed by yeast cells.

In order to use Aequorin as a growth marker, the reporter gene must be permanently expressed (Aequorin is under the control of a constitutive yeast promoter). Then, each cell contains a comparable amount of reporter protein. If the assay is started with the same number of cells per well, at the end of the assay the Aequorin signal detected in each well will be proportional to the growth (i.e. to the new number of cells). Since it is less stable than β-Galactosidase, Aequorin is more accurate to measure growth variations.

The present invention relates to a modified yeast cell containing an Aequorin encoding sequence under the control of a constitutive yeast promoter. In a special embodiment of the invention the Aequorin encoding sequence is SEQ ID NO: 1. In another special embodiment of the invention the constitutive yeast promoter is the Triose Phosphate Isomerase promoter. In another embodiment of the invention another heterologous protein; e.g. a heterologous kinase protein is in addition expressed in the modified yeast cell.

The present invention also relates to the use of the modified yeast cells, e.g. for screening of compounds.

Examples for yeast cells are *Saccharomyces cerevisiae, Schizosaccharomyces pombe* and *candida albicans* which can be modified by introducing heterologous sequences.

In a method for identifying compounds that modulate heterologous protein-mediated growth or compounds that exhibit anti-fungal activity, a modified yeast cell containing an Aequorin encoding sequence under the control of a constitutive yeast promoter is grown under conditions where the Aequorin protein is expressed. The modified yeast cell is incubated with a compound to be tested and the amount of growth in the presence of the compound is determined, preferably in comparison to the amount of growth in the absence of the compound or in the absence of the heterologous protein.

Aequorin proved to be a better marker than β-Galactosidase to evaluate the number of cells per well in a 96-well plate, information expected in a high-throughput growth assay. In the same kind of assay, the toxicity of a compound can also be more easily detected with Aequorin than with β-Galactosidase, maybe because of the high stability of the second.

In another type of test, Aequorin could be utilized to assay toxicity of a hyperactivated kinase.

Additionally, bacterial contamination sometimes occurs in the yeast assay and most of the contaminants physiologically express a β-Galactosidase. The contaminated cultures would give a very strong signal in presence of the β-Galactosidase substrate. The use of Aequorin eliminates the risk of false positives due to contamination.

EXAMPLES

Example 1

Materials and Methods

As a yeast strain W303 MAT a, far::hisG, sst2::$URA3^{FOA}$, fus1::HIS3 was used.

The yeast strain was transformed with the different plasmids according to the Lithium acetate method (Ito et al., 1983).

Example 2

Construction of the Aequorin Expression Vectors

The full length cDNA aequorin gene was amplified by PCR using the chimerical mitochondrial aequorin mtAEQ (where the truncated N-terminus is fused to the human cytochrome C targeting signal (Rizzuto et al., 1992)) as a template. The 5' PCR primer contained the 50 first nucleotides of aequorin wild type sequence and an EcoRI (noted in bold type below) cloning site. The 3' primer did not contain any cloning site.

```
                                         (SEQ ID NO:3)
5' AQWT:
5'-CCG GAA TTC CGG ATG ACA AGC AAA CAA TAC TCA GTC

AAG CTT ACA TCA GAC TTC GAC AAC CC

                                         (SEQ ID NO:4)
3' AQWT:
5'-GGG CCT TAG GGG ACA GCT CCA CCG TAG AGC.
```

The full-length wild type Aequorin coding sequence (FIG. 1) was then cloned in the commercially available yeast expression vector (Ingenius R&D) pYX132 TPI (Triose Phosphate Isomerase promoter, TRP1 marker, CEN), strong constitutive expression vector (FIG. 2);

Example 3

Construction of the β-Galactosidase Expression Vectors

To allow the comparison, LacZ was sub-cloned in the same way than aequorin, into the same expression vector (and without any fusion with the 5' sequence of a endogenous gene as is was often done to increase the expression level (King et al., 1990)).

Figure 3:
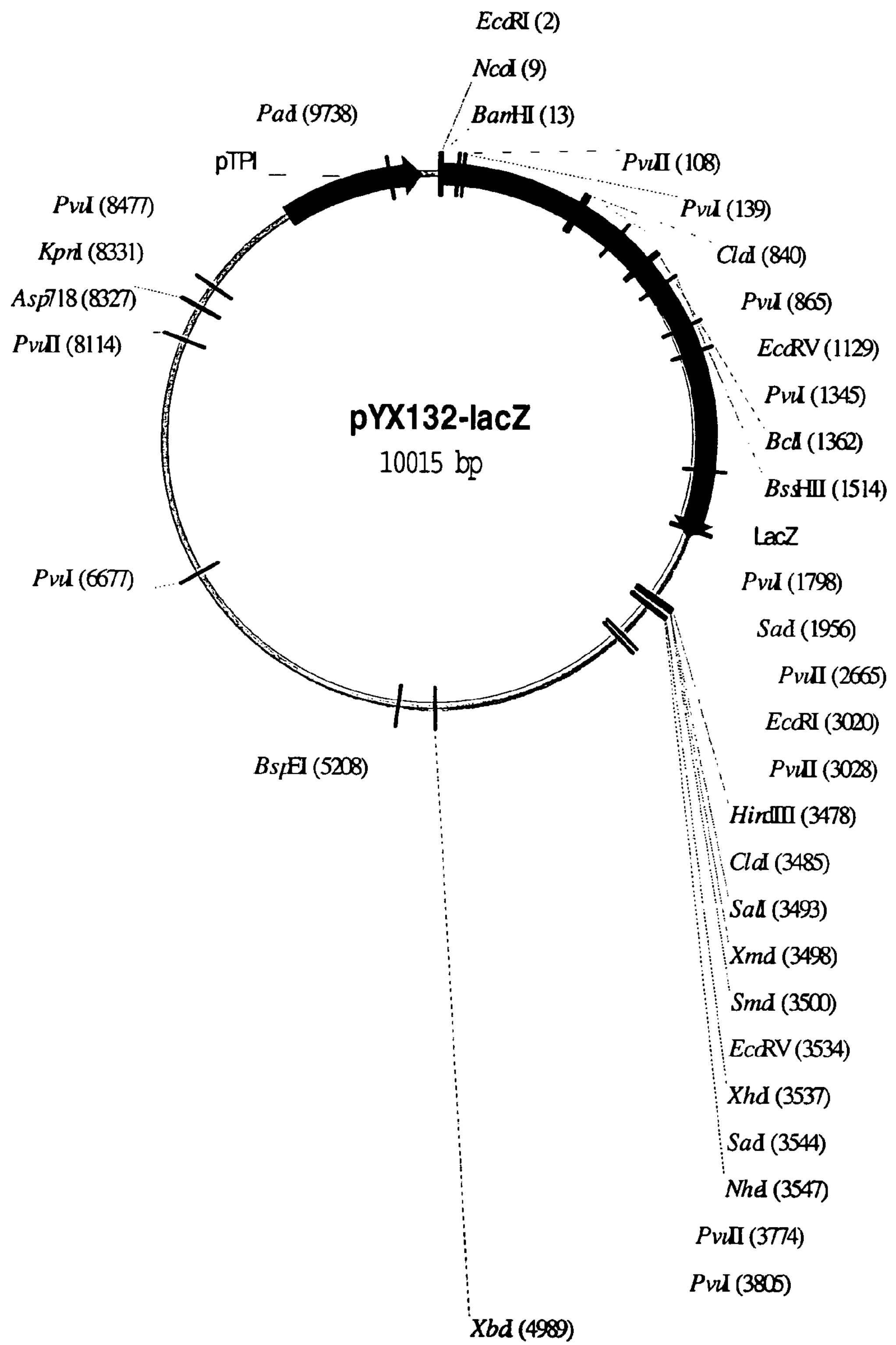
FIG. 3: Restriction map of pYX132TPI-lacZ

The full-length *Escherichia coli* β-Galactosidase gene sequence was cloned in the vector pYX132 TPI (Triose Phosphate Isomerase promoter, TRP1 marker, CEN), strong constitutive expression vector (FIG. 3);

Example 4

Aequorin Detection

The cells are distributed and/or grown in a white 96-well plate, in a volume of 100 μl.

30 minutes before the measurement time point, 10 μl of a 5 μM coelenterazine (Molecular Probes) solution is distributed in each well (to obtain a 0.5 μM final concentration) to load the cells.

The plate is then incubated at 30° C. for the last 30 minutes.

Aequorin detection is made in a luminometer with injecting system (Luminoskan, Labsystems). For each well, immediately after injection of a 10 mM CaCl2 solution (1 M CaCl2 diluted in lysis buffer Y-PER from Pierce), the luminescent signal is integrated for 15 seconds.

To avoid the intermediate step of loading, it is possible to introduce coelenterazine in the medium at the beginning of the assay: coelenterazine is added at a concentration of 0.5 μM.

Example 5

β-Galactosidase Detection

The cells are distributed and/or grown in a white 96-well plate, in a volume of 100 μL.

At the measurement time point, each well receives 100 μl of a β-Galactosidase detection mix (Gal-screen, Tropix).

The plate is incubated for one hour at 28° C.

β-Galactosidase signal is read in a luminometer; the luminescent signal is integrated for 0.5 seconds.

Example 6

Growth Marker: Aequorin Compared to Lacz

Example 6.1

Linearity

The pYX132TPI expression plasmid was chosen because it combines a reproducible number of copies per cell (centromeric replication origin) with a constitutive strong expression level (Triose Phosphate Isomerase promoter (Alber and Kawasaki, 1982)).

Three colonies of the yeast strain transformed with either pYX132TPI-AEQ or pYX132TPI-LacZ plasmids were grown in the appropiate medium (SC Glucose-Trp) to stationary phase and then serially diluted in the same medium (with 0.5 μM coelenterazin for the aequorin strain): from $10^6$ to $10^4$ cells per well. The plate was then shaken at 30° C., 700 r.p.m., for 1.5 hours to re-initiate the exponential growth.

FIGS. 4(*a*) and (*b*) show the difference of linearity obtained with two reporter genes: aequorin would be suitable until 3 to $4.10^5$ cells per well whereas the lacZ signal reaches very rapidly a plateau (linearity only until $10^5$).

Example 6.2

Stability upon Toxicity or Growth Arrest

Two colonies of the yeast strain transformed with either pYX132TPI-AEQ or pYX132TPI-LacZ or empty pYX132TPI plasmids were grown in the appropiate medium (SC Glucose-Trp) to stationary phase and then diluted in three different media:

- SC Glucose-Trp (normal growth medium);
- SC Glucose-Trp containing 100 μM of a toxic compound (Ziprasidone, a potassium channel blocker that shows high toxic effects on *S. cerevisiae*);
- SC Glucose-Ura (the strain will starve because it needs uracile to grow).

The results are shown on FIGS. 5 to 8.

After 5 hours of treatment (FIG. 5 & FIG. 6), the toxic effect was well detectable in a optical density (OD) measurement ($OD_{630}$=0.05 to 0.07 instead of 0.09 to 0.19) as well as with both reporter genes.

- Aequorin showed, for the cells in presence of Ziprasidone, a signal equivalent to the starving cells (10 and 16 r.l.u., respectively) while the normal growth would give a aequorin signal of 138. In other words, aequorin showed a 10 fold difference between toxic treatment and normal growth.
- β-Galactosidase reflected also the toxicity but in a much lower contrast: the normal growth would give a signal of 276 r.l.u. while the Ziprasidone treated cells produce 116 r.l.u. (i.e. only half of the normal signal), and the starving cells give a signal of 64 r.l.u.

After 24 hours treatment (FIG. 7 & FIG. 8), the cells in the medium lacking uracile did not grow, they could recover from the toxicity of Ziprasidone and grow up to $OD_{630}$=0.5-0.7, while the cells in the appropriate medium grew to saturation (i.e. to $OD_{630}$ over 1). Again this effect was better reflected by aequorin:

- with aequorin, after toxic treatment the signal was 50 r.l.u. and after normal growth 175 r.l.u.; that is to say a difference of 3.5 fold;
- the β-Galactosidase numbers for treated or non treated cells were not significantly different (respectively 1923 and 2275 r.l.u.).

This experiment shows that β-Galactosidase is not suitable, in a short assay (5 hours), to show a suffering of the yeast cell. The sensitivity is much higher with aequorin. This result might be due to the high stability of the protein β-Galactosidase.

In a longer assay (24 hours), the difference of sensitivity of the two reporters appears to be even more significant.

Example 7

Screening for Inhibitors of a Human Kinase

A human kinase, potentially a therapeutic target, is modified to become constitutively active. The activated kinase is toxic for the yeast and induces cell death. Both kinase and Aequorin are under the control of a promoter induced only in presence of galactose.

The cells are grown in SC Glucose, rinsed, and then diluted to $10^6$ cells/ml in SC/Glucose or SC/Galactose. After 30 hours incubation at 30° C., coelenterazine is added and the Aequorin signal measured after injection of $Ca^{2+}$, accordingly to the Aequorin detection protocol.

Figure 9:
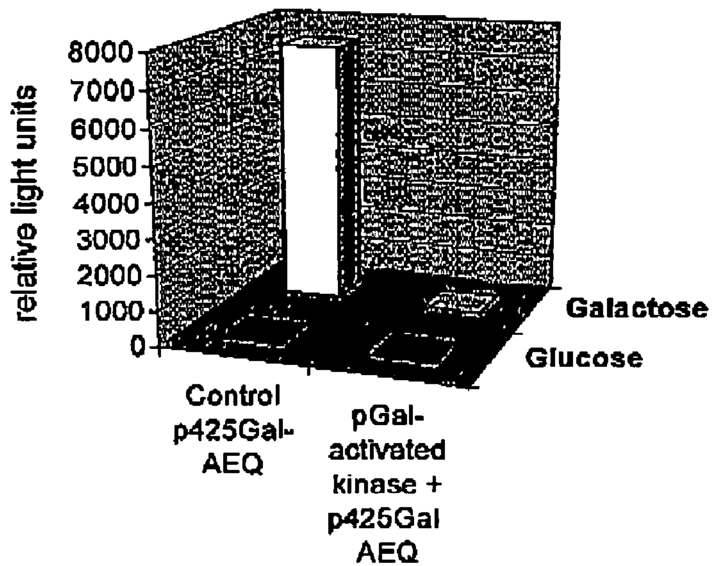
FIG. 9: Results of toxicity detection in a kinase screen
Figure 10:
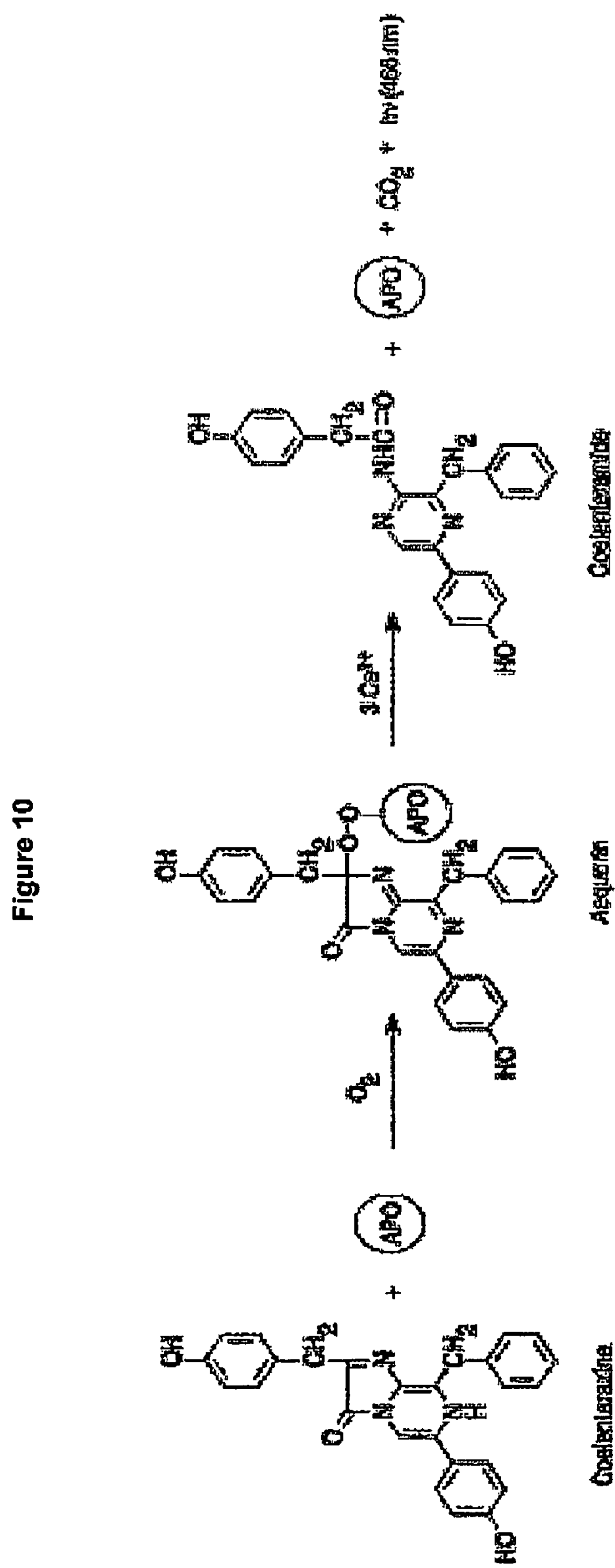
FIG. 10: $Ca^{2+}$-dependent generation of luminescence by the aequorin complex, which contains apoaequorin (APO) and coelenterazine (Ohmiya and Hirano, 1996).

The FIG. 9 shows that in glucose medium, there is a very slide expression of Aequorin but comparable in the two strains.

In galactose medium (both Aequorin and the active kinase are expressed) the Aequorin signal is very high (7457 relative light units) in absence of any toxicity, but disappears completely (0,5 r.l.u.) when the active kinase is expressed.

This example is a preliminary test for set up of a kinase inhibitor screening: the compound which can rescue cell death is selected for its potential inhibitory activity on the kinase.

REFERENCE LIST

Alber T and Kawasaki G (1982) Nucleotide Sequence of the Triose Phosphate Isomerase Gene of *Saccharomyces Cerevisiae*. J Mol Appl Genet 1: pp 419-434.

Brini M, Pinton P, Pozzan T and Rizzuto R (1999) Targeted Recombinant Aequorins: Tools for Monitoring [$Ca^{2+}$] in the Various Compartments of a Living Cell. Microsc Res Tech 46: pp 380-389.

Detheux M (2000) Orphan Receptors: the Quest for New Drug Targets. Innovations in Pharmaceutical Technology 00: pp 27-34.

Iida H, Yagawa Y and Anraku Y (1990) Essential Role for Induced $Ca^{2+}$ Influx Followed by [$Ca^{2+}$]i Rise in Maintaining Viability of Yeast Cells Late in the Mating Pheromone Response Pathway. A Study of [$Ca^{2+}$]i in Single *Saccharomyces Cerevisiae* Cells With Imaging of Fura-2. J Biol Chem 265: pp 13391-13399.

Inouye S, Aoyama S, Miyata T, Tsuji F I and Sakaki Y (1989) Overexpression and Purification of the Recombinant $Ca^{2+}$-Binding Protein, Apoaequorin. J Biochem (Tokyo) 105: pp 473-477.

Ito H, Fukuda Y, Murata K and Kimura A (1983) Transformation of Intact Yeast Cells Treated With Alkali Cations. J Bacteriol 153: pp 163-168.

Johnson F H and Shimomura O (1978) Bioluminescence and Chemiluminescence: Introduction to the Bioluminescence of Medusae, With Special Reference to the Photoprotein Aequorin. Methods Enzymol 57: pp 1-653.

King K, Dohlman H G, Thorner J, Caron M G and Lefkowitz R J (1990) Control of Yeast Mating Signal Transduction by a Mammalian β2-Adrenergic Receptor and Gs Alpha Subunit [Published Erratum Appears in Science 1991 Jan. 11; 251 (4990):144]. Science 250: pp 121-123.

Miller A L, Karplus E and Jaffe L F (1994) Imaging $[Ca^{2+}]i$ With Aequorin Using a Photon Imaging Detector. Methods Cell Biol 40: pp 305-338.

Nakajima-Shimada J, Iida H, Tsuji F I and Anraku Y (1991a) Galactose-Dependent Expression of the Recombinant $Ca^{2+}$-Binding Photoprotein Aequorin in Yeast. Biochem Biophys Res Commun 174: pp 115-122.

Nakajima-Shimada J, Iida H, Tsuji F I and Anraku Y (1991b) Monitoring of Intracellular Calcium in *Saccharomyces Cerevisiae* With an Apoaequorin CDNA Expression System. Proc Natl Acad Sci USA 88: pp 6878-6882.

Ohmiya Y and Hirano T (1996) Shining the Light: the Mechanism of the Bioluminescence Reaction of Calcium-Binding Photoproteins. Chem Biol 3: pp 337-347.

Rizzuto R, Simpson A W, Brini M and Pozzan T (1992) Rapid Changes of Mitochondrial $Ca^{2+}$ Revealed by Specifically Targeted Recombinant Aequorin [Published Erratum Appears in Nature 1992 Dec. 24-31; 360(6406):768]. Nature 358: pp 325-327.

Sheu Y A, Kricka L J and Pritchett D B (1993) Measurement of Intracellular Calcium Using Bioluminescent Aequorin Expressed in Human Cells. Anal Biochem 209: pp 343-347.

Shimomura O and Johnson F H (1978) Peroxidized Coelenterazine, the Active Group in the Photoprotein Aequorin. Proc Natl Acad Sci USA 75: pp 2611-2615.

Stables J, Mattheakis L C, Chang R and Rees S (2000) Recombinant Aequorin As Reporter of Changes in Intracellular Calcium in Mammalian Cells. Methods Enzymol 327: pp 456-471.

Thomas A P and Delaville F (1991) The Use of Fluorescent Indicators for measurements of cytosolic-free calcium concentration in cell populations and single cells., in Cellular Calcium: A Practical Approach (McCormack J G and Cobbold P H eds) pp 1-54.

The invention claimed is:

1. A method of measuring the growth rate of a yeast cell culture, the method comprising:

(a) providing a yeast cell culture wherein the yeast cell comprises an aequorin-encoding deoxyribonucleic acid sequence expressibly linked to a constitutive yeast promoter, said constitutive yeast promoter being a triosephosphate isomerase promoter, (b) incubating the yeast cell culture and (c) measuring the amount of aequorin produced after the cells are lysed and mixed with $Ca^{2+}$ by measuring luminescence wherein the intensity of luminescence indicates the growth rate of said yeast cell culture and wherein the intensity of luminescence is proportional to the growth rate at a cell density of up to $4\times10^6$ cells/ml.

2. A method for determining growth-regulating or toxic effects of a compound on a yeast cell culture, the method comprising:

(a) providing a yeast cell comprising an aequorin-encoding deoxyribonucleic acid sequence expressibly linked to a constitutive yeast promoter, said constitutive yeast promoter being a triosephosphate isomerase promoter, (b) incubating the yeast cell with the compound, (c) measuring the amount of aequorin produced after the cells are lysed and mixed with $Ca^{2+}$ by measuring luminescence wherein the intensity of luminescence indicates the growth rate of said yeast cell culture and wherein the intensity of luminescence is proportional to the growth rate at a cell density of up to $4\times10^6$ cells/ml and (d) comparing the measured amount of aequorin produced with that amount of aequorin produced by a yeast cell of step (a) incubated in the absence of the compound.

* * * * *